United States Patent [19]
Fotinos

[11] Patent Number: 5,976,565
[45] Date of Patent: Nov. 2, 1999

[54] DEVICE FOR TOPICAL TREATMENT OF ACNE AND ITS METHOD OF MANUFACTURE

[75] Inventor: Spiros Fotinos, Athens, Greece

[73] Assignee: Lavipharm Laboratories, Inc., Piscataway, N.J.

[21] Appl. No.: 08/880,099

[22] Filed: Jun. 20, 1997

[51] Int. Cl.[6] .................................................. A61F 9/70
[52] U.S. Cl. ...................... 424/448; 424/404; 424/414
[58] Field of Search ................................ 424/443, 445, 424/446, 449, 404, 448, 414

[56] References Cited

U.S. PATENT DOCUMENTS 5,449,519  9/1995  Wolf et al. ................................ 424/401

OTHER PUBLICATIONS

Product package, Dermatological Sciences Corp. Submission Date Feb. 3, 1999.

*Primary Examiner*—Thurman K. Page
*Assistant Examiner*—D. Faulkner
*Attorney, Agent, or Firm*—Bromberg & Sunstein LLP

[57] ABSTRACT

A patch for topical application of an anti-acne formulation has in various embodiments a backing film, a release layer and at least one adhesive polymeric matrix layer located between the backing film and the release layer. The anti-acne formulation is uniformly distributed throughout one or more polymeric matrix layers and has an anti-acne effective amount of at least two agents selected from the group consisting of an anti-microbial, an antiseptic, an anti-irritant, a keratolytic agent, a hormone, a hormone agonist and a hormone antagonist.

36 Claims, 3 Drawing Sheets

DEVICE FOR TOPICAL TREATMENT OF ACNE AND ITS METHOD OF MANUFACTURE

TECHNICAL FIELD

A delivery device in the form of patch, and method of its manufacture, is provided for the topical treatment of acne and acneiform diseases.

BACKGROUND ART

Acne afflicts 90% of all teenagers but also men and women in their twenties or thirties or may persist throughout adulthood. The process by which acne develops has been described in "New Approaches to Acne Treatment" by W. J. Cunliffe, ed. Martin Dunitz, London, 1989.

Acne vulgaris is a chronic disorder of the pilosebaceous follicles (apparatus) characterized by comedones (blackheads), papules, pustules, cysts, nodules, and often scars, that appear on the most visible areas of the skin particularly on the face, chest, back and occasionally neck, and upper arms.

The pilosebaceous apparatus is largely under the control of endogenous hormones (mainly androgens) which are present in unusually high concentrations in the blood during adolescence and puberty giving rise to an excessive production of sebum. The condition may worsen by a simultaneous increase in the rate of keratinization of the skin's horny layer (the stratum corneum). As the horny cells proliferate, they can form an occlusive plug or comedone which coupled with the increased production of the sebum, represents an ideal medium for the proliferation of the skin resident strains, such as the Gram positive anaerobic bacterium, Propionibacterium acnes.

Eventually, the plugged follicles rupture and allow the discharge of their contents causing local swelling and inflammation. The exposed follicles may darken from the deposition of pigment from damaged cells in the deeper layer of skin.

Acne is a multistage condition and in most severe form leads to hospitalization of the patient and extensive discomfort with long term scarring of the skin. There is a need for improved treatments for acne that will effectively prevent the condition developing to its most severe form and that can be used by majority of the sufferers without adverse effects.

At this time there are numerous treatments available for treating acne but each treatment has unfortunate limitations which it would be desirable to overcome. In most part, treatment of acne is by topical formulations in the form of creams, gels, emulsions or lotions which contain selected agents. These agents include hormones or hormone agonists and antagonists (EP A1 0 563 813 and U.S. Pat. No. 5,439,923), antimicrobial agents (U.S. Pat. No. 4,446,145, GB 2,088,717, GB 2,090,135, GB 1,054,124, U.S. Pat. No. 5,409,917), salicylic acid (U.S. Pat. No. 4,514,385, U.S. Pat. No. 4,355,028, EP A1 0 052 705, FR-A 2,581,542, and FR-A 2,607,498). The problems associated with topical treatment of acne with creams, gels, emulsions and lotions include the lack of precision of application and associated lack of control over precise dose at the target site. Application of a cream, gel, emulsion or lotion results in exposure of an area considerably in excess of that covered by lesion thereby exposing normal healthy skin to the anti-acne formulation. For example salicylic acid is an irritant to normal skin over prolonged exposure and particularly in high concentrations.

Oral administration of anti-acne agents is currently provided for severe cases of acne. These are reviewed in "Acne, A Review of Optimum Treatment" by Sykes N. I. and Webster G. F in Drugs 48, 59–70 (1994). Numerous side effects have been described using oral administration of anti-acne drugs. For example, isotretinoin which is a derivative of vitamin A has associated risks of teratogenicity and may be a risk for women of childbearing age. Oral administration of antibiotics suited for treating acne, may induce the appearance of adverse effects which include abdominal cramps, black tongue, cough, diarrhea, fatigue, irritation of the mouth and other undesirable symptoms.

Salicylic acid in the form of a tacky hydrophilic gel dressing (U.S. Pat. No. 5,258,421) and in combination with pantothenic acid or pantothenic acid derivative in a cleansing pad (PCT WO 93/21899) has been used for treating acne.

In addition, a patch containing cephalosporin has been described in the U.S. Pat. No. 5,409,917 for the treatment of acne using a method for making nicotine patches. Since the patch was not optimized for the special circumstances associated with acne including optimizing the anti-acne agent content and placement of the patch at multiple locations on exposed skin such as the face, the patch has not been adopted as an anti-acne formulation delivery modality.

There is a need therefore for methods and devices for treating patients with acne that have minimum adverse effects, have maximum efficacy and may be simple and comfortable to use.

OBJECTIVES OF INVENTION

The present invention addresses the need for treating acne and acneiform diseases so as to minimize adverse effects and to maximize efficacy of treatment. The present invention is directed to a topical delivery device, in the form of a patch, having a size and thickness suited for prolonged delivery of an anti-acne formulation at a selected site characterized as acneiform. The patch contains at least two agents suited for treating acne.

In a preferred embodiment, a patch is provided for topical application of an anti-acne formulation that includes a backing film, a release layer and a polymeric matrix located between the backing film and the release layer for containing the anti-acne formulation. The formulation includes an effective amount of at least two agents selected from the group consisting of an anti-microbial, an antiseptic, an anti-irritant and an acne therapeutic agent.

In a further embodiment, the acne therapeutic agent is selected from at least one of the group consisting of a keratolytic agent, a hormone, a hormone agonist, and a hormone antagonist.

In a further embodiment of the invention, a method for manufacturing a delivery device for treating acne is provided that includes mixing a single adhesive or a mixture of adhesives and at least one of a keratolytic agent, an antiseptic, an anti-irritant, and a solubilizer so as to form a blend; and laminating the blend on a first side with a release liner and on a second side with a backing film.

In a further embodiment of the invention, a device in the form of a patch for the topical application of an anti-acne formulation is provided that includes a synthetic pressure-sensitive adhesive used as a carrier or polymeric matrix or associated with a carrier or polymeric matrix, said carrier having the anti-acne formulation uniformly distributed therein, characterized in that said anti-acne formulation comprises effective amounts of at least two active ingredients from at least two different groups of active ingredients and in that said at least two different groups are selected from the group comprising keratolytic agents, anti-irritant agents, antiseptic agents, antimicrobial agents, hormones, hormone-agonists, hormone-antagonists and other agents suitable for treating acne.

In another embodiment, a patch for the treatment of acne and acneiform skin diseases includes topically acceptable carriers for topical application, such as acrylics, paper, silicones, cellulosics, moisturizers; antioxidants; and stabilizers; wherein the patch is capable of delivering an effective amount of anti-acne agents to acneiform skin to be treated (i.e. comedones, pustules, papules).

In a further embodiment of the invention, the patch of the invention is capable of prolonged delivery of the formulation, the time range being greater than 4 hours, preferably at least 24 hours, more preferably 8 hours.

In a preferred embodiment of the invention, the patch has a thickness in the range of 0.5 to 2 cm and a thickness in the range of 7 to 24 mils (about 178 to 610 $\mu$m).

BRIEF DESCRIPTION OF THE DRAWINGS

FIG. 2b is a top view of the same patch as in FIG. 2a.

DESCRIPTION OF THE INVENTION

The term topically acceptable carriers, as used herein, means substances substantially lacking toxicity for human tissues.

The term "topical application", as used herein, means directly laying on outer skin.

The term "stable", as used in the specification is defined as possessing a shelf-life that extends for more than several weeks.

The term "effective amount", as used herein, means an amount sufficient to provide an anti-acne effect.

The present invention provides methods and devices for treating patients affected by acne, where the device has been optimized for minimizing adverse effects and for maximizing efficacy and is simple and comfortable to use. The topical treatment of acne and acneiform diseases disclosed herein utilizes a patch to achieve local anti-acne effects that result from the suppression of the proliferation of horny cells and microbes involved in the pathogenicity of acne and reduction in associated inflammation. The patch has been designed so as to effectively deliver anti-acne agents to the stratum corneum (the outermost layer of epidermis, exposed to external environment) and subsequently to penetrate into the pilosebaceous unit (in the dermis) where the acneiform condition originates, while having very limited penetration into the systemic circulation. This is demonstrated by the skin flux permeation study (Example 12 hereafter), which indicates that the amount of salicylic acid that crosses stratum corneum is very small as compared to that of the gel formulation containing 2% of salicylic acid.

In order to ensure that the patch is simple and comfortable to use, a suitable size and thickness of a single patch has been identified. The patch proposed in this invention can be produced in a variety of sizes dependent on the area to be treated (i.e. comedones, papules, pustules). The size of the patch is classified as small being 0.5 to 2 $cm^2$ and large patch up to 40 $cm^2$. Typically, the size of the patch is from 0.5 to 1.3 $cm^2$ and preferably 0.8 $cm^2$.

The patch of the invention is stable and is capable of safe and effective delivery of the anti-acne formulation. For example, the stored patch containing anti-acne agent may remain effective up to two years such that any chemical changes that may occur during storage, but before the predetermined expiration date, are believed to be non-harmful.

Figure 1:
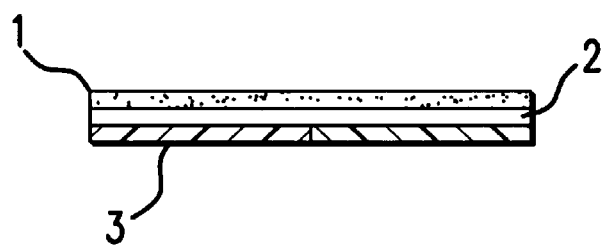
FIG. 1 is a side view of a three layered patch for delivering agents for the treatment of acneiform diseases.

An example of the patch suitable for treating acne is described in FIG. 1. In this embodiment, the patch may include a backing film layer 1, a single synthetic pressure-sensitive adhesive layer 2 and a release liner 3 with the anti-acne formulation contained within the synthetic pressure-sensitive adhesive layer.

Figure 2A:
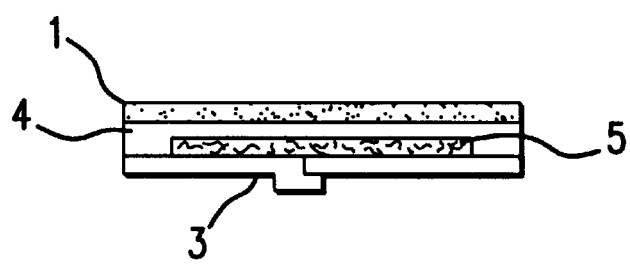
FIG. 2a is a side view of a four layered patch for delivering agents for the treatment of acneiform diseases.
Figure 2B:
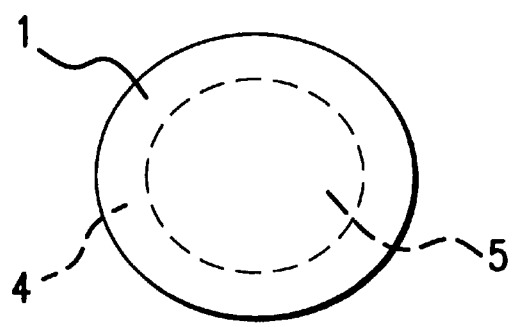

In other embodiments, more than one matrix may be positioned between the release liner and the backing layer (see FIGS. 2a and 2b). According to FIGS. 2a and 2b and Example 4, a patch is described that includes a backing film layer 1, a synthetic pressure-sensitive peripheral adhesive layer 4, a paper matrix and a release liner. The patch may have a paper matrix diameter of ⅝ "(inches) (about 1.6 cm) and/or a peripheral adhesive layer diameter of ⅞ "(about 2.2 cm).

The backing film layer 1 may be made of plastic or fabric or woven or non-woven materials, porous or occlusive. Porous materials are sometimes used since some of the slain resident strains of the bacteria in the pilosebaceous unit are anaerobic.

The backing film layer can be made of any suitable material such as paper; cellophane; plastic films such as polyethylene, polyester, polyurethane, polyvinyl chloride and polyamide; fabrics and metallic foils, which are impermeable and non-reacting with the anti-acne formulation distributed in the adhesive polymeric matrix. The backing film can be composite or transparent or opaque or fleshtoned or aluminized or a combination thereof, with thickness ranging from 1 to 5 mils (about 25 to 130 $\mu$m) typically about 2 to 3.5 mils (about 50–90 $\mu$m) and preferably 3 mils (about 76 $\mu$m), and can be formed from any of CoTran™9720 (3M), Saranex®(Dow Chemicals), Multilam fleshtoned polyester film 1009 (3M), or any other material recognized in the art as having the desired properties.

The patch has an adhesive polymeric matrix 2, which is adjacent to the backing layer and may be made of synthetic adhesives such as acrylics, rubber, silicone, cellulosics, paper or other suitable materials that may have pressure sensitive properties and adhere to the skin directly or through a peripheral adhesive. The adhesive polymeric matrix consists of at least one layer of the adhesive-containing substances and/or other additives. The adhesive polymeric matrix may be composed of more than one layer, but is preferably composed of one layer. The thickness of this adhesive polymeric matrix is in the range of 0.5–30 mils (about 13–760 $\mu$m), typically of 0.5–6 mils (13–152 $\mu$m), preferably 0.5–2.5 mils (about 13–64 $\mu$m) and more preferably 2.5 mils (about 64 $\mu$m). Contained within the adhesive polymeric matrix is an anti-acne formulation including any of keratolytics, anti-irritants, antiseptics, antimicrobials, hormones, hormone-agonists, hormone-antangonists and other agents suitable for treating acne, preferably together with solubilizers.

The adhesive polymeric matrix can be made of inert materials which are further biologically and topically acceptable and compatible with the distributed active substances described above.

Preferably, topically acceptable polymers with adhesion properties may be acrylic-based polymers such as the GELVA® series sold by Monsanto and the DURO-TAK® series sold by National Starch; rubber-based polymers such as DURO-TAK® series sold by National Starch; and silicone-based polymers such as BIO-PSA X7-4302 SILICONE PSA sold by Dow Corning.

The said adhesive polymeric matrix can also be made of paper materials, preferably Whatman filter paper, which is adhered onto the skin through a peripheral adhesive layer. The thickness of such an adhesive polymeric matrix is usually 7 mils (about 178 $\mu$m).

A release liner 3, is placed against the surface of the adhesive polymeric matrix on the surface opposite to the backing layer. The release liner can be made of materials impermeable to any substance dissolved in the said matrix, which is easily stripped off or released prior to the use. The release liner can be made of materials such as polyvinyl chloride, polyester, polyvinylidene chloride, polystyrene, polyethylene, paper etc. coated or not with an adhesive, but preferably with an easy release silicon formulation.

Preferably the release liner is made of a natural, high impact polystyrene film (grade code: 10106 or 15462) sold by REXAM Release or a siliconized polyester film sold by REXAM Release. The thickness of the release liner can range from 3 to 10 mils (about 76 to 250 $\mu$m), or preferably be 10 mils (about 250 $\mu$m).

Preferably, the patch has a size in the range of 0.5 to 2 cm$^2$ and a thickness in the range of 7 to 24 mils (about 178 to 610 $\mu$m).

In an embodiment of the invention, a combination of anti-acne agents has been selected to treat acne. These agents include a keratolytic agent, such as salicylic acid, in conjunction with an anti-irritant, an antiseptic, an antimicrobial agent and/or other acne fighting compounds such as for example urea, allantoin, hydroxyquinoline compounds, for delivery via a patch directly to the area to be treated. The presence of an anti-irritant counteracts the local irritation associated with the application of keratolytics to the skin. The antiseptic limits the growth of organisms which cause the acne. Furthermore, the antimicrobial may enhance the overall anti-acne properties of the compositions in moderate or severe stages of the disease. The use of a solubilizer ensures that the active agents in the patch are in form suited for diffusion from the patch to the skin.

Antimicrobials typically used for topical application can be penicillins, cephalosporins, other beta-lactam compounds, aminoglycosides, tetracyclines, erythromycin, antifungal agents, etc. and a combination thereof. Preferably, antimicrobial agents used for topical application onto acneiform skin are erythromycin, tetracycline, clindamycin, cephalosporin.

Antiseptics typically used for topical application onto acneiform skin are triclosan (Irgasan DP 300), phenoxy isopropanol, resorcinol, chlorhexidine, povidone and iodine.

Keratolytic agents typically used for topical application onto acneiform skin are salicylic acid, benzoyl peroxide, sulphur, retinoic acid and any of a number of fruit acids and alpha hydoxy acids.

Anti-irritants typically used for the topical application onto acneiform skin are $\alpha$-bisabolol, farnesol, chamomile extract and glycyrrhetinic acid.

Solubilizers used in the anti-acne formulation of the present invention include any of glycerol, propylene glycol, polyalcohols, sorbitol and sorbitol derivatives, preferably sorbitan monooleate.

Compositions of the present invention can also comprise other topically acceptable agents such as solvents, antioxidants, moisturizers etc.

According to a preferred embodiment, the invention provides a device as described above, which comprises, related to the total weight of the carrier and the formulation:

one or more keratolytic agent(s), each in an amount of 0.1 to 10.0% w/w, preferably of 0.1 to 2.0% w/w and more preferably of 0.6% w/w;

one or more anti-irritant agent(s),each in an amount of 0.01 to 5.0% w/w, preferably of 0.01 to 3.0% w/w and more preferably of 1.0% w/w;

one or more antiseptic agent(s), each in an amount of 0.05 to 2.0% w/w, preferably of 0.1 to 1.0% w/w and more preferably of 0.3% w/w; and one or more solubilizer(s), each in an amount of 0.1 to 5% w/w, preferably of 1 to 3.0% w/w and more preferably of 2% w/w.

This invention is further illustrated by the examples. Examples are not to be construed as being a limitation on the scope of invention, which scope is defined by the appended claims. The examples are conducted using salicylic acid, as keratolytic agent, in an amount of 0.1 to 2% w/w together with an anti-irritant such as ($\alpha$-bisabolol in 0.01 to 3% w/w, an antiseptic such as triclosan (Irgasan DP 300) in 0.1 to 1% w/w and a solubilizer such as sorbitan monooleate in 0.1 to 5% w/w, having all of them dispensed in variety of adhesive polymeric matrices. Controlled delivery is achieved over a period of at least 4 hours, preferably over a period of at least 24 hours and more preferably over a period of at least 8 hours.

EXAMPLE NO. 1

Preparation of polymeric matrix and delivery device in the form of patch.

A composition of the adhesive polymeric matrix used in the preparation of a patch for the topical treatment of acne and acneiform skin diseases contains salicylic acid as keratolytic agent as described in Table 1.

TABLE 1

Composition of the single adhesive delivery system

| COMPONENT | QUANTITY % w/w (on a dry basis) |
|---|---|
| $\alpha$-Bisabolol[1] | 1.0 |
| Irgasan DP 300[2] | 0.3 |
| Salicylic acid | 0.6 |
| Sorbitan Monooleate | 2.0 |
| Gelva ® 737 | 96.1 |

[1]$\alpha$-Bisabolol is 6-methyl-2-(4-methyl-3-cyclohexen-1-yl)-5-hepten-2-ol
[2]Irgasan DP 300 is 2,4,4'-trichloro-2'-hydroxy diphenyl ether A method for producing the patch having the above composition is as follows:

Salicylic acid (0.6 g), Irgasan DP 300 (0.3 g), $\alpha$-bisabolol (1.0 g), sorbitan monooleate (2.0 g) are added to 293.88 g of Gelva® 737 multi polymer resin solution (total solids content of about 32.7%), and the mixture is stirred at ambient temperature until all the ingredients have dissolved. The mixture is allowed to stand for several minutes so as to remove air bubbles.

The adhesive mixture was formulated into a patch system as follows:

Using an appropriate coating device (square tool steel Multi Clearance Applicator, sold by BYK Gardner) with a 5 or 10 mil (about 130–250 µm) casting gap, a layer of adhesive mixture was coated onto a siliconized polyester film and dried in an oven at 76–78° C. for 15–18 minutes. A breathable polyurethane film (Bertek Medfilm 390) was then laminated onto the adhesive film. The system was then delaminated and further laminated on an easy release silicon polystyrene film (REXAM Release). The final thickness of the dried polymeric matrix was, then, 3 to 5 mils (about 76–130 µm).

The multi-layer laminate was then cut to form a patch of circular shape with nominal size of 1 cm$^2$ (actual size of 0.8 cm$^2$) and thickness of 7 to 18 mils (about 178–457 µm).

EXAMPLE NO. 2

Preparation of adhesive polymeric matrix

The procedure of Example 1 is repeated to prepare the adhesive polymeric matrix. The adhesive used in this example is the acrylic-based polymer GELVA®788. The patch, thus produced, finally has a circular shape of 1 cm$^2$ and thickness of 8 to 24 mils (about 203–610 µm).

EXAMPLE NO. 3

Preparation of adhesive polymeric matrix containing a mixture of adhesives

The composition of the adhesive polymeric matrix described in this Example, in the specified amounts, is presented in Table 2

TABLE 2

| Composition of the mixed adhesive delivery system | |
|---|---|
| COMPONENT | QUANTITY % w/w (on a dry basis) |
| α-Bisabolol | 1.0 |
| Irgasan DP 300 | 0.3 |
| Salicylic acid | 0.6 |
| Sorbitan Monooleate | 2.0 |
| Duro-Tak ® 87-2287: Duro-Tak ® 87-2353 (1:9 ratio by weight in dry coating) | 96.1 |

A homogeneous mixture is obtained by mixing 18.95 g of Duro-Tak® 87-2287 acrylic solution (total solids content of about 50.7%) and 238.92 g of Duro-Tak® 87-2353 acrylic solution (total solids content of about 36.2%). To this mixture of adhesives, salicylic acid (0.6 g), α-bisabolol (1.0 g), Irgasan DP 300 (0.3 g), sorbitan monooleate (2.0 g) are added and the mixture is stirred at ambient temperature until all the ingredients are dissolved. The mixture is, then, kept aside for several minutes to have the air bubbles completely removed.

The adhesive mixture is formulated into a patch system as follows:

Using an appropriate coating device with a 5 mil (about 130 µm) applicator gap, a layer of adhesive mixture is coated onto a siliconized polyester film. The coating is left to dry in an oven at 80° C. for 17 minutes and then laminated using an occlusive polyethylene film.

The process ends with cutting the multi-layer laminate to a patch of circular shape, size of 1 cm$^2$, and thickness of 7.5 to 20 mils (about 190–500 µm) which is finally pouched in a flexible, pouching laminate film composed of paper, low density polyethylene, aluminium and Surlyn®.

EXAMPLE NO. 4

Preparation of a delivery device in the form of patch containing a plain adhesive layer and a polymeric matrix with and without adhesive properties In this Example, substances such as antimicrobials, antiseptics, keratolytics, anti-irritants and solubilizers are distributed in a polymeric matrix in which the polymers may or may not have adhesive properties.

The procedure of preparing this patch is presented as follows:

To 10 g ethanol AR, salicylic acid (0.1 g), (α-bisabolol (0.1 g), Irgasan DP 300 (0.03 g) and sorbitan monooleate (0.2 g) are added and the mixture is stirred until all the ingredients are dissolved.

Pieces of Whatman filter paper are impregnated with 3 ml of the above ethanolic solution and left to drain at ambient temperature. The impregnated paper pieces are, then, dried in an oven at 40° C. for 5 minutes and finally cut into a desirable size and shape (i.e. circular shape of ⅝" diameter or area of 5 cm$^2$).

Siliconized polyester films are coated with a plain, acrylic-based adhesive such as Duro-Tak® 87-2287 or Duro-Tak® 87-2353. The bilayer system is dried in an oven at for 15 minutes and, then, laminated with a polyethylene film such as CoTran™ 9720. The whole system is cut into a desirable size and shape (i.e. circular shape of ⅞" diameter or area of 7 cm$^2$).

The polyester film is removed and, onto exposed laminate, the impregnated paper is placed in a co-centric order. Finally the multi-layer system is coated on a polystyrene film, which can be scored on the backside (see FIGS. 2a and 2b).

EXAMPLE NO. 5

Preparation of a delivery device in the form of patch as in Example No 4 containing an additional adhesive layer.

The procedure of Example 4 is repeated to prepare a patch, in which the exposed laminate is coated on a polystyrene film coated completely or partially with a plain adhesive.

EXAMPLE NO. 6

Stability of the produced patch

The patch proposed in the present invention will remain stable for two years. Methods such as composite assay for salicylic acid and physical tests (such as 90° dynamic adhesive strength peel test for matrix patch from stainless steel plate as in "Test Methods for Pressure Sensitive Adhesive Tape" developed by The Technical Committee of the Pressure Sensitive Tape Council, 11th Edition) are used to determine its stability over this time.

Figure 3:
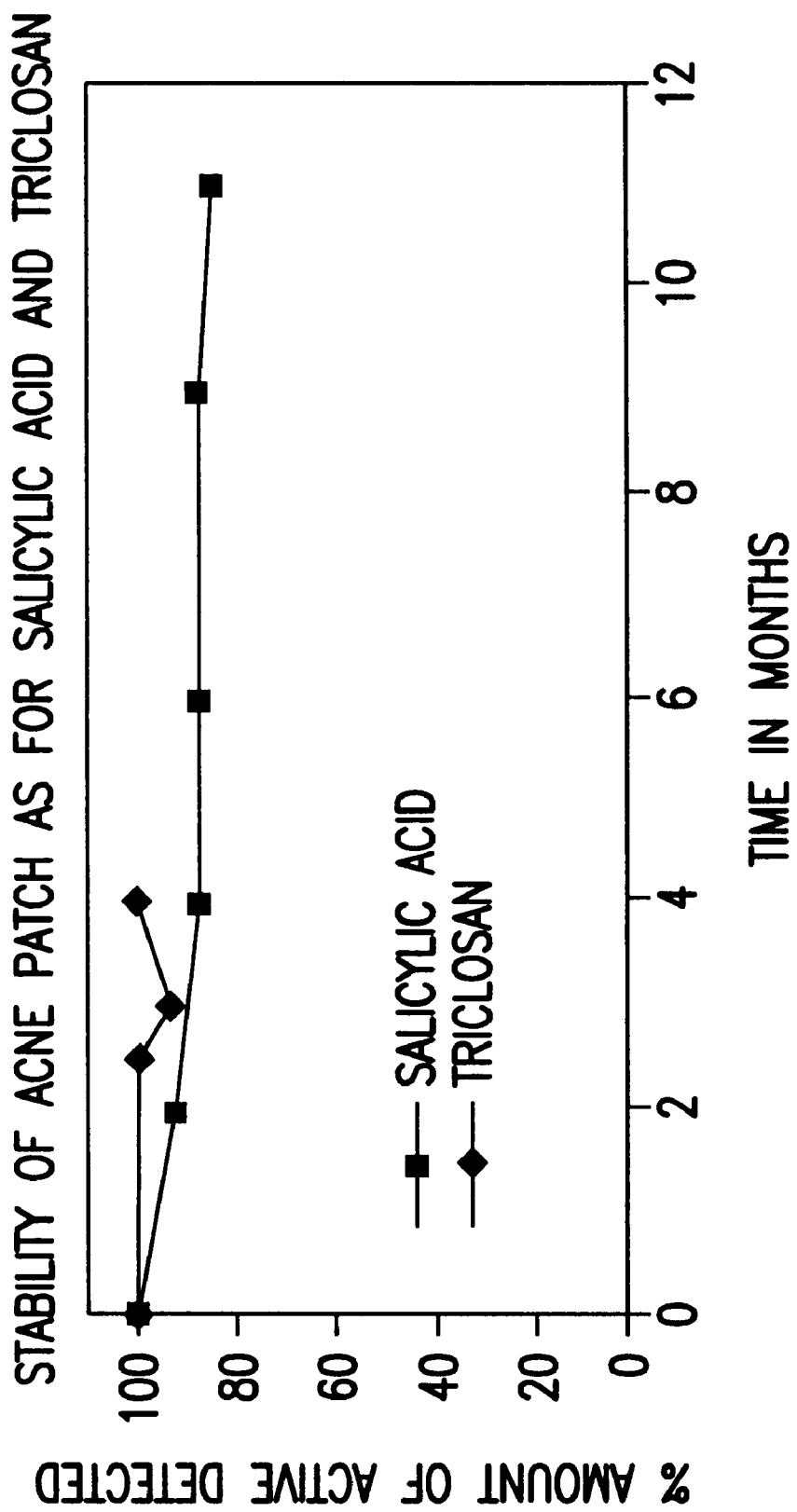
FIG. 3 shows the stability of the patch of the invention as for salicylic acid and triclosan.

Furthermore the stability of the proposed patch was examined under ambient conditions. The results expressed as % amount of salicylic acid and triclosan detected in the patch over the time are presented in FIG. 3.

EXAMPLE NO. 7

Patch depletion analysis

The patch produced is designed to release its content at 4, 6, 10, and up to 24 hours after application. To determine the rate and extent of the release for salicylic acid from the patch, a patch depletion analysis is performed.

EXAMPLE NO. 8

Primary Dermal Irritation Study

A Primary Dermal Irritation Study, in compliance with the FDA Requirements per 21 CFR 58, was performed using patches containing salicylic acid, as disclosed in preferred embodiments, in order to identify the potential irritation or corrosive effects that result from the exposure of rabbit skin to the test material.

The fur of six healthy New Zealand rabbits was clipped as close to the skin as possible at the test site twenty-four hours prior to the application of the test material.

The test material was applied to both intact and abraded skin, and each test area was covered with an 1 inch square gauze patch hold in place with non-irritating tape. The skin exposed to the test material for a period of twenty-four hours and examinations of the animals for signs of erythema, edema, and any lesions or other toxic effects were made at thirty to sixty min after patch removal and, then, at seventy-two hours.

The study showed that the patches produced a very slight erythema with some flaking skin at some test sites but no edema. In addition, no other toxic effects were observed during the study.

The Primary Irritation Score as estimated was 0.54 which indicates that the test material is not considered to be a primary skin irritant as defined in 16 CFR 1500.3 (c) (4).

EXAMPLE NO. 9

Delayed Contact Hypersensitivity test—Modified Buehler sensitization test.

A Delayed Contact Hypersensitivity test, in compliance with the FDA Requirements per 9 CFR 2.31, was performed using patches containing salicylic acid, as disclosed in the preferred embodiments, in order to determine the capacity of the test substance to induce a systemic hypersensitivity response.

The Experimental Procedure Consisted of Two Phases:

1. Induction Phase

One group of 20 guinea pigs was exposed to the test material patch and one group of 10 guinea pigs was exposed to Dinitrochlorobenzene (DNCB), a known sensitizer. The day before dosing, the animals were clipped free of hair, as close to the skin as possible, using electric clippers.

The test material patch was applied to the clipped area of each of the 20 guinea pigs and held in place with a non-irritant tape. The patches were left in place for 6 hours and then removed. The test sites were scored for erythema at 24 and 48 hours post application. This procedure was repeated at the same site once a week for the next two weeks for a total of three 6-hour exposures. After the last patch application the animals remained untreated for approximately two weeks.

To the positive control group of 10 guinea pigs, a solution of 0.75% of DNCB in 50% ethanol was applied and scored as previously described.

In the following tables the individual scores for the test material patch and the positive control are presented.

TABLE 3

Individual animal scores for the test material.
Erythema

| Animal | Week 1 | | Week 2 | | Week 3 | |
|---|---|---|---|---|---|---|
| | 24 h | 48 h | 24 h | 48 h | 24 h | 48 h |
| 1 | 0 | 0 | 0 | 0 | 0 | 0 |
| 2 | 0 | 0 | 0 | 0 | 0 | 0 |
| 3 | 0 | 0 | 0 | 0 | 0 | 0 |
| 4 | 0 | 0 | 0 | 0 | 0 | 0 |
| 5 | 0 | 0 | 0 | 0 | 0 | 0 |
| 6 | 0 | 0 | 0 | 0 | 0 | 0 |
| 7 | 0 | 0 | 0 | 0 | 0 | 0 |
| 8 | 0 | 0 | 0 | 0 | 0 | 0 |
| 9 | 0 | 0 | 0 | 0 | 0 | 0 |
| 10 | 0 | 0 | 0 | 0 | 0 | 0 |
| 11 | 0 | 0 | 0 | 0 | 0 | 0 |
| 12 | 0 | 0 | 0 | 0 | 0 | 0 |
| 13 | 0 | 0 | 0 | 0 | 0 | 0 |
| 14 | 0 | 0 | 0 | 0 | 0 | 0 |
| 15 | 0.5 | 0 | 0 | 0 | 0 | 0 |
| 16 | 0 | 0 | 0 | 0 | 0 | 0 |
| 17 | 0 | 0 | 0 | 0 | 0 | 0 |
| 18 | 0 | 0 | 0 | 0 | 0 | 0 |
| 19 | 0 | 0 | 0 | 0 | 0 | 0 |
| 20 | 0 | 0 | 0 | 0 | 0 | 0 |

There was no erythema noted for the test material during the three induction phases.

TABLE 4

Individual animal scores for the positive control.
Erythema

| Animal | Week 1 | | Week 2 | | Week 3 | |
|---|---|---|---|---|---|---|
| | 24 h | 48 h | 24 h | 48 h | 24 h | 48 h |
| 1 | 0.5 | 0 | 0.5 | 0 | 2 | 1 |
| 2 | 1 | 0.5 | 1 | 1 | 2 | 1 |
| 3 | 1 | 0 | 1 | 0.5 | 1 | 1 |
| 4 | 0.5 | 0 | 1 | 0.5 | 2 | 2 |
| 5 | 1 | 0.5 | 0.5 | 0 | 1 | 1 |
| 6 | 1 | 0 | 1 | 0.5 | 2 | 1 |
| 7 | 0.5 | 0 | 1 | 1 | 2 | 1 |
| 8 | 1 | 0 | 1 | 1 | 2 | 1 |
| 9 | 1 | 0.5 | 1 | 1 | 1 | 1 |
| 10 | 1 | 0.5 | 1 | 0.5 | 2 | 1 |

During this test, animals showed from no to faint and faint confluent erythema.

2. Challenge Phase

After the two week rest, the test group and the positive control group were challenged on naive sites. The test material was applied to the test group and the DNCB to the positive control group. The procedure employed was as described above, except skin evaluations were made at 24, 48 and 72 hours post application. The results are presented in the following tables.

TABLE 5

Individual animal scores for the test material.
Erythema

| Animal | 24 h | 48 h | 72 h |
|---|---|---|---|
| 1 | 0 | 0 | 0 |
| 2 | 0 | 0 | 0 |
| 3 | 0 | 0 | 0 |

TABLE 5-continued

Individual animal scores for the test material.
Erythema

| Animal | 24 h | 48 h | 72 h |
|---|---|---|---|
| 4 | 0 | 0 | 0 |
| 5 | 0 | 0 | 0 |
| 6 | 0 | 0 | 0 |
| 7 | 0 | 0 | 0 |
| 8 | 0 | 0 | 0 |
| 9 | 0 | 0 | 0 |
| 10 | 0 | 0 | 0 |
| 11 | 0 | 0 | 0 |
| 12 | 0 | 0 | 0 |
| 13 | 0 | 0 | 0 |
| 14 | 0 | 0 | 0 |
| 15 | 0.5 | 0 | 0 |
| 16 | 0 | 0 | 0 |
| 17 | 0 | 0 | 0 |
| 18 | 0 | 0 | 0 |
| 19 | 0 | 0 | 0 |
| 20 | 0 | 0 | 0 |

During challenge phase, no erythema was noted in the test material group at any point.

TABLE 6

Individual animal scores for the positive control.
Erythema

| Animal | 24 h | 48 h | 72 h |
|---|---|---|---|
| 1 | 1 | 0.5 | 0.5 |
| 2 | 1 | 0.5 | 0.5 |
| 3 | 1 | 1 | 0.5 |
| 4 | 1 | 0.5 | 0.5 |
| 5 | 1 | 1 | 0.5 |
| 6 | 1 | 0.5 | 0 |
| 7 | 1 | 0.5 | 0.5 |
| 8 | 2 | 1 | 0.5 |
| 9 | 2 | 1 | 0.5 |
| 10 | 1 | 1 | 0.5 |

During this test, animals showed from no to faint and faint confluent erythema.

EXAMPLE NO. 10

Repeated Insult Patch Test for Contact Sensitization and Photosensitization.

The purpose of this study was to determine the cutaneous and contact sensitization and photosensitization in human volunteers of the patch containing salicylic acid as described in the preferred embodiments of the present invention, in order to claim the "hypoallergenicity" of the product.

Forty (40) healthy volunteers of both sexes, aged 20–55 years old, were included in the study.

1. Induction Phase

In this part, repeat insult patch tests in combination with maximization test were used. On intact skin of the upper back of the forty volunteers, a 1% solution of sodium lauryl sulfate was applied. The test product was, then, applied and held with a non-irritant tape. The test material was left on, for 48 hours and the site was read 30 minutes after the removal of the patch. A new patch was then reapplied to the same site. New patches were applied 3 times per week and assessments were carried out at 48 hour post removal. Repeated application of the patches using this method was continued for three weeks (total ten applications).

Additional patche tests were used to determine the contact photosensitization of the patch. During the induction phase and in parallel with the repeat patch tests, the patch tests sited were irradiated on five occasions with a solar stimulator or UVA (5 Joules) after removal of five repeated patches (serial). The phototoxic potential of the test patch was evaluated on hour, 6 and 24 hours after a single treatment.

2. Challenge Phase

After the end of the three week period a rest period of fifteen days followed. At the end of the rest period patch tests were performed as follows:

The sodium lauryl sulfate solution was first applied to the back followed by the test material patch. In the challenge test, the patch was removed at 48 hours post application and assessments were carried out at 24, 48 and 72 hours post application. During the challenge phase a second test patch was performed at another site and after its removal the site was irradiated with UVA (5 Joules). Readings were performed at 72 and 96 hours post application.

The assessments for both phases were carried out by the same investigator and under the same conditions. Scoring was based on the standard ICDRG scale. The results were negative for both phases and thus the test patch can be considered as "Hypoallergenic" and "Dermatological Tested".

EXAMPLE NO. 11

Repeated Irritation Test in Humans.

The purpose of this study was to provide a quick and simple indication of the potential irritancy for the test patch. Because of the lower sensitivity of human skin to irritants, versus animal model, testing in man is generally performed by repetive application of the test patch.

The study involved 20 volunteers, male or female (15–50 years old), whose upper backs were free from any skin problems.

The test material patch was initially applied in the upper back of the volunteer for 24 hours, held with a non-irritant Scanpor tape, and then removed. One hour upon removal, the skin site was gently wiped with a moist wool ball and graded. The test material application was repeated at the same site, 24 hours later. The test material application continued for 20 days (total of 10 applications with a rest period over the weekends).

The results showed no sight of erythema, edema or exudation induced by the test patch and thus the product can be considerd as "Non irritant".

EXAMPLE NO. 12

Permeability of the anti-acne patches.

To evaluate the local effect of the anti-acne patches according to the invention, the transdermal absorption (flux) of the salicylic acid from the adhesive matrix of the invention was determined in vitro by using human cadaver skin, according to the procedure described by Franz T., in Percutaneous absorption on the relevance of the in vitro data, J. Invest. Derm. 64, 190–195, 1975.

For in vitro flux studies, the stratum corneum of human cadaver skin was used. Using fresh, post-mortem skin samples, the stratum corneum was separated from the skin by the technique described by Kligman, A. M. Et al in Preparation of the isolated sheets of the human stratum corneum, Arch. Derm. 88, 702, 1963.

Figure 4A:
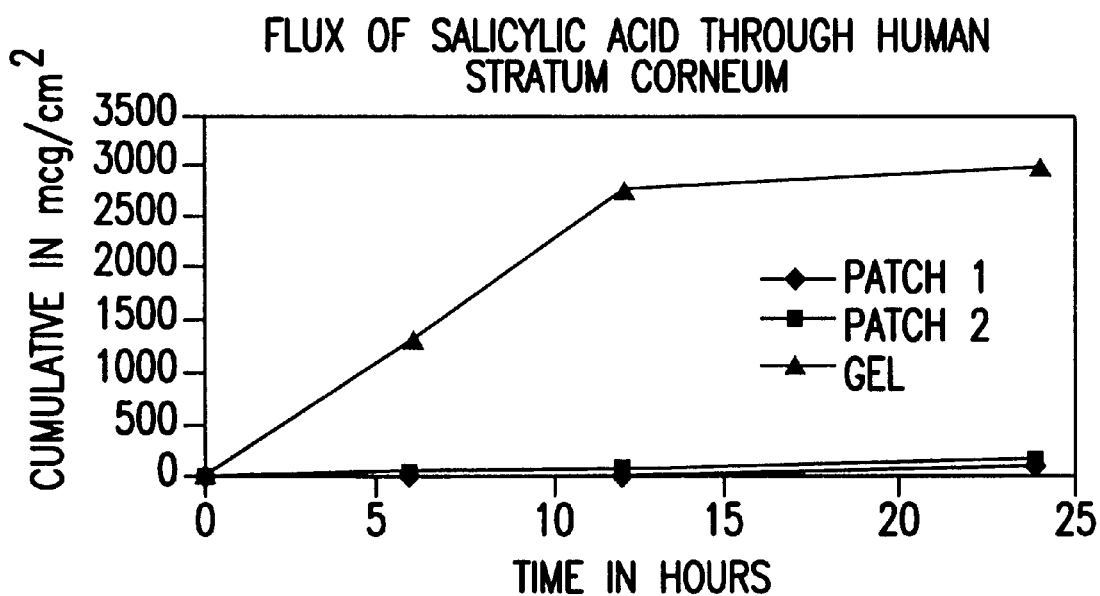
FIG. 4a shows the flux of salicylic acid through human stratum corneum as concerns two patches according to the invention and a gel.
Figure 4B:
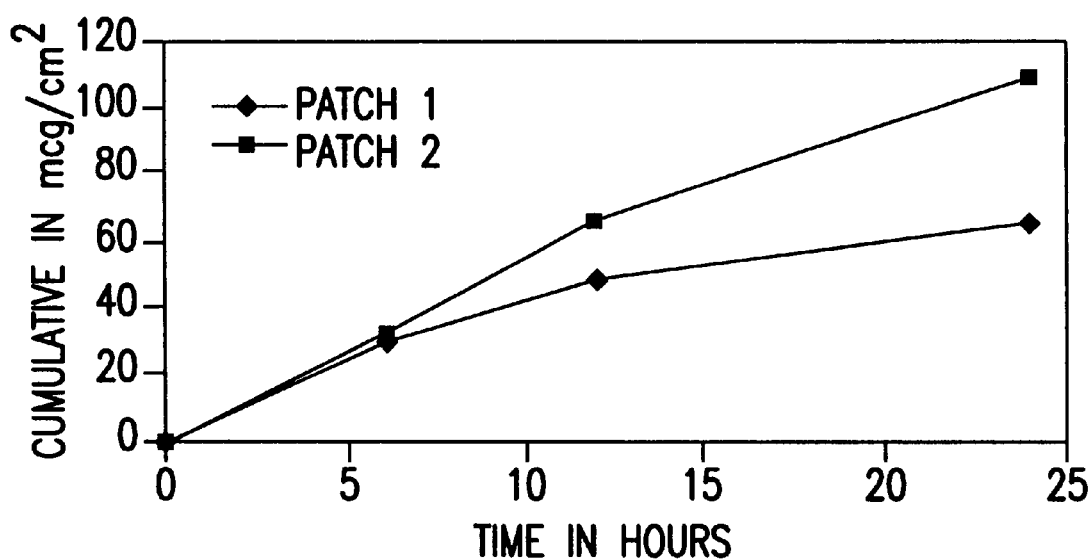
FIG. 4b is an enlargement of FIG. 4a as concerns the two Patches of the invention.

A comparative study of skin flux determination (expressed as cumulative amount of salicylic acid permeation per unit of area at any time) between the anti-acne patch of the invention (Patch 1), the same patch but having an adhesive matrix of double thickness (Patch 2) and a reference gel formulation containing 2% of salicylic acid (Gel) is presented in FIG. 4 [FIG. 4a and FIG. 4b].

The results showed a very limited penetration for the antiacne patch of both adhesive matrix thickness as compared to that of the reference gel formulation, assuring thus the local effect of the proposed anti-acne patch.

I claim:

1. A patch for topical application of an anti-acne formulation, comprising: a backing film, a release layer and at least one adhesive polymeric matrix layer located between the backing film and the release layer, wherein the anti-acne formulation is uniformly distributed throughout one or more of the polymeric matrix layers, the formulation comprising an anti-acne effective amount of at least two agents selected from the group consisting of an anti-microbial, an antiseptic, an anti-irritant, a keratolytic agent, a hormone, a hormone agonist and a hormone antagonist.

2. The patch according to claim 1, having a size and thickness suited for prolonged association with a skin surface.

3. A patch according to claim 1, wherein the at least one polymeric matrix layer includes a polymeric matrix layer in contact with one or more adhesive polymer layers.

4. A patch according to claim 2, wherein the adhesive polymer is a synthetic pressure sensitive adhesive polymer.

5. A patch according to claim 3, wherein the one or more adhesive polymeric layers are formed from a synthetic pressure sensitive polymer.

6. A patch according to claim 2, wherein the adhesive polymer is formed from one or more polymers selected from the group consisting of acrylic based polymers, rubber based polymers and silicone based polymers.

7. A patch according to claim 3, wherein the polymeric matrix layer is formed from a paper matrix and the one or more adhesive polymer layers are formed from at least one polymer selected from the group consisting of acrylic based polymers, rubber based polymers and silicone based polymers.

8. A patch according to claim 1, wherein the backing layer is occlusive.

9. A patch according to claim 1, wherein the backing layer is breathable.

10. A patch according to claim 1 wherein the anti-acne formulation further comprises one or more solubilizers.

11. A patch according to claim 10, wherein the solubilizer is selected from the group consisting of glycerol, propylene glycol, polyalcohols, sorbitol and sorbitol derivatives.

12. A patch according to claim 10, wherein each solubilizer is present in an amount in the range of 0.1 to 5% w/w.

13. A patch according to claim 1, wherein the solubilizer is sorbitan monooleate.

14. A patch according to claim 1, wherein the keratolytic agent is selected from the group consisting of salicylic acid, benzoyl peroxide, sulfur, retinoic acid, a fruit acid and alpha hydroxy acids.

15. A patch according to claim 14, wherein each keratolytic agent is present in an amount in the range of 0.1–10%.

16. A patch according to claim 1, wherein the anti-acne formulation includes salicylic acid.

17. A patch according to claim 1, wherein the anti-acne formulation includes one or more anti-irritant agents selected from the group consisting of α-bisabolol, farnesol, glycyrhetinic acid and chamomile extract.

18. A patch according to claim 17, wherein each anti-irritant agent is present in an amount in the range of 0.1–5% w/w.

19. A patch according to claim 1, wherein the anti-acne formulation includes α-bisabolol.

20. A patch according to claim 1, wherein the anti-acne formulation includes one or more antiseptic agents selected from the group consisting of triclosan povidone, iodine, resorcinol, phenoxy isopropanol and chlorhexidine.

21. A patch according to claim 20, wherein each antiseptic agent is present in an amount in the range of 0.05–2.0% w/w.

22. A patch according to claim 1, wherein the anti-acne formulation includes one or more antimicrobial agents, selected from the group consisting of erythromycin, tetracycline, cephalosporin and clindamycin.

23. A patch according to claim 2 wherein the prolonged association of the patch with the skin is at least 4 hours.

24. A patch according to claim 2, wherein the size of the patch is in the range 0.5–2cm$^2$ and a thickness in the range of 178–210 μm.

25. A method for manufacturing a delivery device for treating acne, comprising:
    (a) mixing at least one polymer with a solubilizer and an anti-acne formulation wherein the anti-acne formulation comprises at least two agents selected from the group consisting of a keratolytic agent, an antiseptic, an anti-irritant, an anti-microbial, a hormone, a hormone antagonist and a hormone agonist so as to form a blend; and
    (b) laminating the blend on a first side with a release liner and on a second side with a backing film.

26. A method for manufacturing a delivery device for treating acne comprising
    (a) impregnating a paper with an anti-acne formulation comprising at least two agents selected from the group consisting of a keratolytic agent, an anti-microbial, an antiseptic, an anti-irritant, a hormone, a hormone agonist and a hormone antagonist.
    (b) placing the impregnated paper in contact with a synthetic pressure sensitive peripheral adhesive layer; and
    (c) laminating the impregnated paper in contact with the adhesive layer on a first side with a release liner and on a second side with a backing film.

27. A method according to claim 26, wherein the keratolytic agent is salicylic acid.

28. A method according to claim 26, wherein an antiseptic is triclosan.

29. A method according to claim 26, wherein the anti-irritant is α-bisabolol.

30. A method according to claim 26, wherein the paper further includes a solubilizer and the solubilizer is sorbitan monoleate.

31. A patch for topical application of an anti-acne formulation, comprising; a backing film, a release layer, and at least one polymeric matrix layer located between the backing film and the release layer, wherein the anti-acne formulation is uniformly distributed throughout at least one of the polymeric matrix layers, the formulation comprising an effective amount of an antiseptic, an anti-irritant, and a keratolytic agent.

32. A patch according to claim 31, wherein the antiseptic is Irgasan DP 300.

33. A patch according to claim 31, wherein the anti-irritant is α-bisabolol.

34. A patch according to claim 31, wherein the keratolytic agent is salicylic acid.

35. A patch according to claim 31, wherein the antiseptic is Irgasan DP 300, the anti-irritant is α-bisabolol, and the keratolytic agent is salicylic acid.

36. A patch for topical application of an anti-acne formulation, comprising: a backing film, a release layer and a paper layer located between the backing film and the release layer, wherein the anti-acne formulation is uniformly distributed throughout the paper layer, the formulation comprising an anti-acne effective amount of at least two agents selected from the group consisting of an anti-microbial, an antiseptic, an anti-irritant, a keratolytic agent, a hormone, a hormone agonist and a hormone antagonist.

* * * * *

UNITED STATES PATENT AND TRADEMARK OFFICE
CERTIFICATE OF CORRECTION

PATENT NO. : 5,976,565
DATED : November 2, 1999
INVENTOR(S) : Fotinos

It is certified that error appears in the above-identified patent and that said Letters Patent is hereby corrected as shown below:

Please add the following references (A-Y) to the front of the patent:

| Ref. No. | Document No. | Issue Date | Name | Class |
|---|---|---|---|---|
| AA | 3,896,789 | 07/29/75 | Trancik | 128/2 |
| AB | 4,073,291 | 02/14/78 | Marvel | 128/155 |
| AC | 4,355,028 | 10/19/82 | Kligman et al. | 424/230 |
| AD | 4,568,343 | 02/04/86 | Leeper et al. | 604/896 |
| AE | 4,839,174 | 06/13/89 | Baker et al. | 424/447 |
| AF | 5,258,421 | 11/02/93 | Lorenz et al. | 523/111 |
| AG | 5,409,917 | 04/25/95 | Robinson et al. | 514/200 |
| AH | 5,439,923 | 08/08/95 | Cullinan | 514/324 |
| AI | WO 85/03434 | 08/15/85 | PCT | |
| AJ | WO 92/10154 | 06/25/92 | PCT | |
| AK | WO 93/21899 | 11/11/93 | PCT | |
| AL | WO 94/04184 | 03/3/94 | PCT | |
| AM | WO 95/08330 | 09/16/94 | PCT | |
| AN | WO 97/12598 | 04/10/97 | PCT | |
| AO | WO 98/00117 | 01/8/98 | PCT | |
| AP | 0 052 705 | 06/02/82 | EP | |
| AQ | 0 299 758 | 07/14/88 | EP | |
| AR | 0 307 187 | 03/15/89 | EP | |
| AS | 0 506 300 A2 | 09/30/92 | EP | |
| AT | 0 563 813 A1 | 10/06/93 | EP | |

UNITED STATES PATENT AND TRADEMARK OFFICE
CERTIFICATE OF CORRECTION

PATENT NO. : 5,976,565
DATED : November 2, 1999
INVENTOR(S) : Fotinos

It is certified that error appears in the above-identified patent and that said Letters Patent is hereby corrected as shown below:

| AU | 0 598 606 A1 | 05/25/94 | EP |
|---|---|---|---|
| AV | FR 2 581 542 | 11/14/86 | FR |
| AW | FR 2 607 498 | 06/03/88 | FR |
| AX | Acne A Review of Optimum Treatment, Sykes, Jr. et al., Practical Therapeutics, Drug 48(1):59-70, 1994 | | |
| AY | Physician's Desk Reference, Tsumura Medical | | |

Signed and Sealed this

Nineteenth Day of September, 2000

Attest:

Q. TODD DICKINSON

Attesting Officer     Director of Patents and Trademarks